United States Patent [19]

Shelburne

[11] Patent Number: 4,888,276

[45] Date of Patent: Dec. 19, 1989

[54] METHOD AND COMPOSITION FOR THE DIAGNOSIS OF LYME DISEASE

[75] Inventor: Charles E. Shelburne, Brooklyn Park, Minn.

[73] Assignee: Minnesota Mining and Manufacturing Company, St. Paul, Minn.

[21] Appl. No.: 879,153

[22] Filed: Jun. 26, 1986

[51] Int. Cl.$^4$ ................ G01N 33/569; G01N 33/577
[52] U.S. Cl. ....................... 435/7; 435/172.2; 435/240.27; 436/548; 530/387
[58] Field of Search ............... 436/501, 536, 948; 435/7, 29, 810, 803, 172.2, 240.27; 530/387

[56] References Cited

U.S. PATENT DOCUMENTS

| | | | |
|---|---|---|---|
| 3,654,090 | 4/1972 | Schuurs et al. | 195/103.5 |
| 3,817,837 | 6/1974 | Rubenstein et al. | 195/103.5 |
| 4,016,043 | 4/1977 | Schuurs et al. | 195/103.5 |
| 4,233,402 | 11/1980 | Maggio et al. | 435/7 |
| 4,275,149 | 6/1981 | Litman et al. | 435/7 |
| 4,584,268 | 4/1986 | Ceriani et al. | 435/7 |

OTHER PUBLICATIONS

Bosler et al, p. 12, Second International Symposium on Lyme Disease and Related Disorders, Compendium of Abstracts, Hygiene Institute of the University of Vienna, 1985.
Burgess, p. 13, Second International Symposium on Lyme Disease and Related Disorders, Compendium of Abstracts, Hygiene Institute of the University of Vienna, 1985.
Barbour et al, J. Inf. Dis. 152:478-484 (1985).
Barbour et al, p. 24, Second International Symposium on Lyme Disease and Related Disorders, Compendium of Abstracts, Hygiene Institute of the University of Vienna, 1985.
Wilske et al, p. 25, Second International Symposium on Lyme Disease and Related Disorders, Compendium of Abstracts, Hygiene Institute of the University of Vienna, 1985.
Wilkinson, pp. 117-122, Lyme Disease, First International Symposium, The Yale J. Biol. Med., 1984.
Steere et al, New England J. Med. 308:733-740 (1983).
Steere et al, pp. 107-110, Lyme Disease, First International Symposiu, The Yale J. Biol. Med., 1984.
Barbour, pp. 71-75, Lyme Disease, First International Symposium, The Yale J. Biol. Med., 1984.
Beck et al, J. Inf. Dis. 152:108-117 (1985).
Barbour et al, Infect. Immun. 41:795-804 (1983).
Laemmli, Nature, 227:680-685 (1970).
Towbin et al, Proc. Nat. Acad. Sci. 76, 4350-4354 (1979).
Tom G. Schwan et al., "The Urinary Bladder, a Consistent Source of *Borrelia burgdorferi* in Experimentally Infected White-Footed Mice (Peromyscus leucopus)", *Journal of Clinical Microbiology*, vol. 26, No. 5, pp. 893-895 (May 1988).
Jorge L. Benach et al., "A Murine IgM Monoclonal Antibody Binds an Antigenic Detrminant in Outer Surface Protein A, an Immunodominant Basic Protein of the Lyme Disease Spirochete", *The Journal of Immunology*, vol. 140, 265-272, No. 1 (1988).
Alan J. Barbour et al., "Lyme Disease Spirochetes and Ixodid Tick Spirochetes Share a Common Surface Antigenic Determinant Defined by a monoclonal Antibody", *Infection and Immunity*, vol. 41, No. 2, pp. 795-804 (1983).
Alan G. Barbour et al., Biological Abstracts, vol. 82 (1986).
Johnson et al., (J. Clin. Microbiol., 20 (6):1099-1101 (1984).
Coonrod, (Amer. J. Med. 75(1B):85-91 (1983).
Isenberg and D'Amato, Chapter 4 in *Manual of Clinical Microbiology*, Lennette et al., eds., 4th ed. (1985), pp. 730-735.
*Zinsser Microbiology*, 18th ed., pp. 730-734, Joklik, et al., eds, Appleton-Century Crofts, Norwalk, CT (1984), pp. 24-35.

*Primary Examiner*—Esther M. Kepplinger
*Attorney, Agent, or Firm*—Donald M. Sell; Walter N. Kirn; Philip M. Goldman

[57] ABSTRACT

A reliable, rapid, inexpensive and noninvasive method is provided for the diagnosis of Lyme disease by the detection of antigens of the spirochete responsible for that disease, *Borrelia burgdorferi*, in the urine of an affected individual.

6 Claims, No Drawings

METHOD AND COMPOSITION FOR THE DIAGNOSIS OF LYME DISEASE

TECHNICAL FIELD

This invention relates to the diagnosis of Lyme disease by the detection of organisms associated with that disease.

BACKGROUND ART

Lyme disease is a systemic tick-borne illness, first reported in the U.S. in the early 1970's, and characterized by a distinctive skin lesion, erythema chronicum migrans (ECM), which is frequently accompanied by headache, stiffness, fever, joint pain, malaise and fatigue. If untreated the disease can also be characterized by the subsequent development of neurological, cardiac and arthritic complications.

The etiological agent believed to be responsible for Lyme disease is a spirochete bacteria first isolated in 1982 from *Ixodes dammini* ticks. The spirochete has since been named *Borrelia burgdorferi*. Various subspecies and strains of this organism have been identified, but their interrelationship has still not been finally determined.

While the primary vector for the disease seems to be the aforementioned tick, Bosler reports the detection, by dark-field microscopy, and culturing of *B. burgdorferi* in the urine of the rodent *Peromyscus leucopus*, and suggests that urine may be a vehicle for non-tick transmission of the disease (p. 12, Second International Symposium on Lyme Disease and Related Disorders, Compendium of Abstracts, Hygiene Institute of the University of Vienna, 1985, hereinafter "1985 Symposium"). Similarly Burgess (1985 Symposium, p. 13) suggests that contact exposure between dogs can result in infection in an experimental setting.

Efforts are ongoing in the scientific community to characterize various isolates from the disease in order to identify different strains of *B. burgdorferi*, and to ascertain the relationship of their differences with the different clinical manifestations of the disease that are found around the world.

Such efforts frequently involve characterization, e.g., by the use of monoclonal antibodies, of the various major protein constituents of *B. burgdorferi*, see e.g., Barbour et al, J. Inf. Dis. 152:478-484 (1985), Barbour (185 Symposium, p. 24) and Wilske (1985 Symposium, p. 25).

Lyme disease is typically diagnosed based on the results of serological and/or clinical findings. Serological findings generally involve assays for the presence of antibodies to *B. burgdorferi* in the sera of patients suspected of having the disease. See, e.g., (Wilkinson, pp. 117-122, Lyme Disease, First International Symposium, The Yale J. Biol. Med., 1984 (hereinafter "1984 Symposium")).

Clinical assessment of Lyme disease is currently the more common means of diagnosing the disease and is most often accomplished by finding a history of ECM and other symptoms associated with the disease. Misdiagnoses of the disease are a problem in view of the close similarity of Lyme disease with other diseases, and because of other factors, e.g., late, sub-clinical, or variable expression of symptoms.

There exists a need for a reliable, rapid, inexpensive and non-invasive method for the diagnosis of Lyme disease. There are many situations in the diagnosis and treatment of Lyme disease where even a reliable test having a low level of false positives would be extremely valuable by itself, and particularly if used in conjunction with other tests that could be used to eliminate the false positives, or with clinical findings to identify the true positives.

Researchers have attempted to correlate the presence of the disease with the identification of *B. burgdorferi* in various body tissues or fluids, e.g., by histological and/or cultural evaluation of samples. Such evaluations can be performed, for instance, by microscopy or by the recovery, i.e., isolation and cultivation, of the organism from tissues or fluids.

*B. burgdorferi* has been isolated and cultivated from the blood, skin, and cerebrospinal fluid of patients with Lyme disease. See, e.g., Steere et al, New England J. Med. 308:733-740 (1983) and Steere et al, 1984 Symposium, pp 107-110. The isolation and cultivation of *B. burgdorferi* is itself frequently a difficult, time-consuming and problematic undertaking however, see, e.g., A. G. Barbour, 1984 Symposium, pp. 71-75. The identity of the recovered organisms as being *B. burgdorferi* was verified in Steere et al (1983) by their reactivity with a monoclonal antibody that had been made against the original isolate of the organism responsible for Lyme disease.

In both references of Steere et al the researchers were unable to isolate any B. burgdorferi spirochetes from either lymph-node aspirates or the urine of patients having Lyme disease.

SUMMARY OF THE INVENTION

The present invention provides a method for detecting an antigen of an organism associated with Lyme disease in an individual that is capable of indicating not only the presence or absence of such an antigen, but also capable of indicating the species or strain of the organism providing the antigen. Surprisingly, applicants have discovered that antigens of such organisms are present in the urine of infected individuals, and that such antigens can be detected early enough in the course of Lyme disease to enable effective treatment of the disease, i.e., before the development of the aforementioned complications.

The invention provides a method for detecting the presence of an antigen of an organism associated with Lyme disease which comprises the steps of:

(a) combining a human urine sample or fraction thereof with antibodies specific for at least one antigen of the organism, wherein any of the antigen present in the urine binds to the antibodies to form an antigen-antibody complex; and (b) detecting the presence of the complex.

Typically the presence of the complex will be compared with the presence of complex in the urine of individuals free of the organism or with other standards or controls.

The method of the present invention provide a reliable, rapid, inexpensive and non-invasive means for the detection of such antigens, in a manner that can enable the tailoring and monitoring of an effective therapeutic regimen.

DETAILED DESCRIPTION

The presence or amount of at least one antigen of an organism associated with Lyme disease is detected in urine. Typically, if necessary, the presence or amount of antigen detected can be compared to the presence or amount of antigen detected in a sample of urine from an individual free of Lyme disease. The antigen may be free of other materials, may be a fragment of a larger molecule or antigen, or may be associated with other antigens or structures, including intact, viable cells.

Preferably the antigen will be one provided by the lipopolysaccharide ("LPS") component of the cell wall of the organism as described, e.g., in Beck et al, J. Inf. Dis. 152:108–117 (1985), or will be provided by one of the major protein classes of the cell membrane of the organism, e.g., B. burgdorferi cellular proteins having apparent molecular weights of 31,000 ("31k") or 34,000 ("34k"), also known, respectively, as "OspA" and "OspB", as determined by polyacrylamide gel electrophoresis and described in Barbour et al, J. Inf. Dis. 152:478–484 (1985) and references cited therein. The disclosures of both Beck et al and Barbour (1985) are hereby incorporated by reference.

The antigen may be specific for one strain, sub-species or species of the organisms associated with Lyme disease, or may be specific for desired groups of strains, sub-species or species. It is only required that the antigen detected is provided by an organism that is associated with Lyme disease, i.e., that the presence of the antigen provides information of diagnostic relevance to the presence, stage or course of Lyme disease. It is currently believed that such organisms are those classified as B. burgdorferi, and that this species is indeed the causative agent of Lyme disease.

In one preferred embodiment of the invention an antigen is detected that is common to all or most members of the species B. burgdorferi. In this way the detection of a single antigen can serve as a comprehensive assay for the presence of that species. In another preferred embodiment one or more antigens are detected, e.g., by a battery of antibodies in a manner that will be able to distinguish between members of the species B. burgdorferi as well as, in sum, detect the presence of all members of that species.

While any receptor may be employed that is specific for the antigenic site of interest, for the most part the receptor will be an antibody, either polyclonal or monoclonal, and while any immunoglobulin may be employed, for the most part IgG will be employed. Similarly, either whole antibodies or fragments thereof may be employed. Single monoclonal antibodies may be employed, or mixtures of antibodies can be employed, including mixtures of monoclonal antibodies or mixtures of polyclonal antibodies. The number and type of antibodies that are employed will depend upon the antigenic site and number of different antigens that are to be detected. The antibody composition will typically be free of non-specific antibodies, i.e., antibodies specific for antigens other than the desired antigens.

The antigens can be detected by preparing antibodies to the intact cell, cell membrane, or antigens of interest and then screening against a number of different cells or cellular antigens. Particularly, one can screen the antibodies by combining them with antigens from a variety of cells different from the cell of interest, particularly where the antigens are bound to a support allowing for ready separation between antibodies that do not bind and antibodies that do bind. One can then further purify the antibodies by combining them with the antigens of interest that are bound to a support and then releasing the antibodies by employing various solutions, such as sodium isocyanate or acetic acid at a concentration sufficient to break down the antigen-antibody complex and allow recovery of the antibody.

Antibodies to antigens of B. burgdorferi, including monoclonal antibodies, can be prepared according to methods known in the art, as disclosed in the Examples herein and, e.g., in Barbour et al, Infect. Immun. 41:795–804 (1983), the disclosure of which is hereby incorporated by reference.

The particular manner in which the presence of B. burgdorferi antigens is detected is not significant in this invention, so long as the method provides the desired degree of sensitivity and reliability. A number of different types of assays exist having a variety of protocols and labels. For the most part, the commonly available assays for detecting specific determinant sites are competitive protein binding assays or immunoassays, where antibodies or fragments thereof are employed. As illustrative of the various assays, are assays described in U.S. Pat. Nos. 3,654,090, 3,817,837, 4,233,402, 4,275,149 and 4,584,268.

In view of the wide diversity of protocols, the specific protocols will not be described. Common to the assays is the formation of a reagent solution containing labeled antibody or labeled antigen. The reagent solution will contain, in addition to the labeled component, other additives, such as buffers, e.g., phosphate, tris, barbital, or the like, normally at concentrations in the range of about 0.01 to 10 mM, the concentration being sufficient to maintain a pH in the range of about 6 to 9, more usually 7 to 8 during the assay. Other additives include preservatives, e.g., sodium azide, inert protein, e.g., serum albumin, sodium chloride, detergents, or the like, which aid in preserving the labeled component, enhancing the formation of the antigen-antibody complex, preventing non-specific binding, or unlabeled component, or the like.

A suitable protocol for detecting antigens according to the method of the present invention is accomplished by electrophoresis of the urine sample, for example on SDS-polyacrylamide gel, using methods known in the art, such as the method of Laemmli, Nature, 227:680–685 (1970). The fractions separated can be transblotted onto nitrocellulose using such known methods as that of Towbin, et al, Proc. Nat. Acad. Sci. 76, 4350–4354 (1979). The nitrocellulose blots are then probed with a selected monoclonal antibody. The antigen-antibody complexes are detected using alkaline phosphatase-conjugated anti-mouse antibodies that react with a Nitroblue tetrazolium/5-bromo-4-chloroindolyl phosphate substrate. The color change indicating the presence of the B. burgdorferi antigen in the blot is readily observed and confirmed by both immunoreactivity and molecular weight. The disclosures of both Laemmli and Towbin et al are hereby incorporated by reference.

A preferred protocol to detect the presence of antigens in urine is by the use of an enzyme linked immunosorbent assay (ELISA) as described, e.g., in U.S. Pat. No. 4,016,043, the disclosure of which is hereby incorporated by reference. ELISA is an assay commonly used to detect both cellular and soluble antigens. Incorporating monoclonal antibodies into such an assay imparts greater specificity to the method. The urine samples are diluted with 5 to 10% SDS-Tris buffer, placed in multiple-well microtiter plates having nitrocellulose membranes ("Millititer", Millipore Corp.) and buffer is added. In order to solubilize the constituents of the urine and avoid clogging, e.g., of nitrocellulose membranes, the urine is preferably boiled, e.g., for 5 to 10 minutes before dilution and plating. The plates are treated, e.g., with 2% bovine serum albumin in buffer to prevent non-specific binding of the antibody to the wells and monoclonal or polyclonal antibody is added as a diluted buffer solution, e.g., 2% bovine serum albumin in 0.1M Tris, pH 8.0, and incubated. The wells are then washed with buffer and anti-mouse antibody conjugated to an enzyme such as alkaline phosphatase is added and the wells are again incubated, e.g., at room temperature such as 20° C. Excess antibody is removed by washing with buffer, and the plates are developed with a combination of enzyme substrate and color indicator until a color change is noted. A variety of substrates are available for use with alkaline phosphatase, e.g., those resulting in color formation or the production of fluorescent light. Other enzymes suitable for use in the assay are, for example, peroxidase and beta-galactosidase.

There will be a variety of situations where the urine of a patient can be assayed to detect the presence of *B. burgdorferi* antigens. In the original diagnosis, where a patient is suspected of having Lyme disease, the urine can be simply screened to detect the presence of such antigens. This test can be used in conjunction with other tests, to enhance the confidence level of a diagnosis of Lyme disease.

The detection of antigen-antibody complex in a sample from an individual suspected of having Lyme disease is typically compared to the presence or amount of complex that is or would be detectable in a similar sample from an individual not having the disease, i.e., compared to a background level of the complex. Suitable methods for making such comparisons are well known to those skilled in the art and include running parallel samples from non-diseased individuals and/or the appropriate use of other standards, controls and the like.

If necessary, urine samples showing positive results in the method of the invention can be either correlated with clinical or serological findings as discussed previously, or can be further evaluated biochemically and/or immunologically to eliminate the possibility of false positives. Further biochemical and/or immunological evaluations include, e.g., electrophoresis and transblotting of the resultant gels as described herein.

Depending on the specificity of the antigen detected for particular strains of *B. burgdorferi*, the results of this test can be used to tailor a therapeutic regimen involving antibiotics. Where Lyme disease has been treated, the presence of residual *B. burgdorferi* infection can be determined by further analysis of the urine.

Urine can be obtained and prepared for assay by any means known in the art that do not interfere with the detection of *B. burgdorferi* antigens. Preferably urine will be obtained by a conventional "clean catch" method. The urine can also be processed, e.g., fractioned, extracted, diluted, concentrated, centrifuged, filtered, dialyzed, buffered and the like, in any way that does not interfere with the method of the invention.

The labeled antibodies will normally be supplied as a lyophilized powder in combination with conventional stabilizers and other additives, including buffers, neutral salts, bulking agents, inert proteins, detergents, e.g., non-ionic detergent, and other additives associated with the nature of the lbel, e.g., substrates for enzyme. These additives will be present in varying amounts, with the antibodies being present in about 0.005 to 5 weight percent, preservatives in about 0.001 to 1 weight percent, neutral salt in about 0 to 15 weight percent, protein in about 0 to 10 weight percent and the remainder bulking agent. The labeled antibody will normally be combined with various excipients, which may serve as extenders and aid in handling and stabilization of the labeled antibody.

Usually, the labeled antibodies will be provided as a kit in combination with controls to produce a standard curve. The controls will have the antigen usually formulated with minor amounts of additives, such as inert protein, non-ionic detergents, e.g., Triton X-100, buffer, preservatives or the like. Also included will be bulking agents, e.g., mannitol. The minor additives will range from about 0.001 to 2 weight percent. The antigen will be present in varying amounts to provide the desired concentration on dissolution into a prescribed volume.

EXAMPLES

The following examples are given to illustrate, but not limit, the scope of this invention.

EXAMPLE 1

Production of Monoclonal Antibodies to *B. burgdorferi*

Five female Balb/C mice (Charles River, Andover, MD) were immunized twice with $10^7$ strain B-31 *B. burgdorferi* (ATCC Accession No. 35210, Rockville, MD) at 14 day intervals intraperitoneally. Sixteen days later they were immunized a single time intravenously and sacrificed three days later by cervical dislocation. The spleens were removed and the splenic leukocytes mixed with the NS-1 mouse myeloma at a leukocyte to myeloma cell ratio of 4:1. The combined cells were centrifuged, the supernatant aspirated and 35% polyethelyene glycol ("PEG", Aldrich Chemicals, Milwaukee, WI) added. The cells were then centrifuged at $800 \times g$ for five minutes, allowed to stand for an additional three minutes and the PEG removed by aspiration. The cells were then washed to remove the residual PEG and cultured overnight in HEPES buffered Dulbecco's Modified Eagle's Medium (Irvine Scientific, Santa Anna, CA) with 10% fetal calf serum (Armour Pharmaceuticals, Chicago, IL). The next day the cells were plated at $7.5 \times 10^5$ cells/ml in the same medium supplemented with hypoxanthine, thymine and aminopterin ("HAT" medium, Sigma Chemical, St. Louis, MO) in microtiter wells. When growth became apparent in individual wells the cells were expanded and the supernatant tested for antibody using an enzyme linked immunoassay.

Monoclonal antibodies prepared as described above were evaluated to determine their reactivity with various *B. burgdorferi* strains including nine strains isolated from human sources, two from animals and one from a tick.

The strains tested were electrophoresed on SDS-polyacrylamide gels using the method of Laemmli, U.K. Nature 227:680-685 (1970). Duplicate gels were run, one for staining with Coomassie blue to detect total proteins and one for transblotting onto nitrocellulose according to the method of Towbin et al, Proc. Nat. Acad. Sci. 76:4350-4354 (1979).

The nitrocellulose blots were probed with one of the monoclonal antibodies being evaluated. The antigen-antibody complexes on nitrocellulose were detected using alkaline phosphatase conjugated anti-mouse antibodies that reacted with a Nitroblue tetrazolium (NBT)/5-bromo-4-chloroindolyl phosphate substrate.

Three monoclonal antibodies that were found to form antigen-antibody complexes with each of the nine *B. burgdorferi* strains evaluated were chosen in view of their favorable growth characteristics, and in view of the fact that it was determined that one monoclonal antibody bound to the 31k (OspA) protein, one bound to the 34k (OspB) protein, and one bound to the lipopolysaccharide band of each of the nine strains. The identity of the lipopolysaccharide band of the electrophoretic gel was confirmed by extraction of LPS according to the method of Beck et al, J. Inf. Dis. 152:108-117 (1985). A hybridoma cell line producing monoclonal antibody binding the 34k protein has been deposited with the American Type Culture Collection, Rockville, MD, and has been assigned ATCC Accession No. HB9126.

EXAMPLE 2

Detection of *B. burgdorferi* in Urine Spiked with the Organism-Sensitivity of the Monoclonal Antibody Assay Frozen *B. burgdorferi* (0.1 ml) cells in saline ($10^{10}$/ml) were resuspended in a mid-stream clean catch sample of human urine (1.0 ml). One hundred μl of 5% sodium dodecyl sulfate ("SDS") in Tris buffer (pH 8.3) was added to lyse the organisms and solubilize their constituents. The concentration of bacteria was then adjusted to $10^8$/ml with either additional urine or 20% methanol in Tris buffer, pH 8.3. Sequential 10-fold dilutions of the bacterial lysates in either urine or Tris-methanol from $10^7$ to $10^3$ organisms/ml were prepared and 100 μl samples were added to triplicate wells of 96-well "Millititer" (Millipore Corp., Bedford, MA) plates. The samples were pulled through by vacuum and the remaining sites blocked with 2% bovine serum albumin ("BSA") in Tris buffer. The wells were then washed three times with phosphate buffered saline-Tween 20 (0.5%) (PBS-Tween 20) (3×250 μl) and 100 μl of diluted monoclonal antibody was added to each well. After one hour incubation the antibodies were removed and the unbound material washed off by 3 additional washes with PBS-Tween 20. One hundred μl of peroxidase-labeled goat anti-mouse IgG was added to each well, incubated an additional hour and unbound material removed with 3 additional washes with PBS-Tween 20. Enzyme substrate solution (100 μl) was added to each well, followed by 50 μl of 2.5M $H_2SO_4$ 5 minutes later and the optical density at 490 nm determined for each well.

The results in TABLE 1 show clearly that *B. burgdorferi* antigens are detectable in urine by monoclonal antibodies to both the 31k and 34k cellular proteins, and can be diluted with either additional urine or buffer, indicating that the binding of antibody is not of a non-specific nature. Under the particular conditions used there was slightly better sensitivity in samples diluted with buffer as opposed to Tris-Methanol, indicating that perhaps the antigen is bound to the nitrocellulose membrane more effectively in the former.

TABLE 1

| log bacteria /ml | O.D. 490: 31k protein urine | 31k protein Tris-MeOH | 34k protein urine | 34k protein Tris-MeOH |
|---|---|---|---|---|
| 7 | .260 | .370 | .510 | .340 |
| 6 | .410 | .190 | .490 | .270 |
| 5 | .180 | .090 | .320 | .111 |
| 4 | .020 | .000 | .130 | .000 |

TABLE 1-continued

| log bacteria /ml | O.D. 490: 31k protein urine | 31k protein Tris-MeOH | 34k protein urine | 34k protein Tris-MeOH |
|---|---|---|---|---|
| 3 | .000 | .000 | .000 | .000 |

EXAMPLE 3

Spiked Human Urine

Urine samples of 10 normal donors and urine from a kidney transplant patient and an SLE patient undergoing acute nephritic crisis were assayed both before and after being spiked with $10^7$ organisms, using an ELISA assay and a monoclonal antibody to the 31k protein as prepared in Example 1. Samples were diluted 1:10 in 250 mM Tris, pH 8.4, 20% methanol, and placed in wells of a "Millititer" plate. The wells were washed once with PBS-Tween 20, and treated with 400 μl per well of 2% bovine serum albumin in 0.1M Tris, pH 8.0, to prevent non-specific binding of antibody to the wells. The wells were washed twice with PBS-Tween 20, and 50 μl of monoclonal antibody (diluted 1:2000 in PBS-Tween 20) was added and allowed to incubate for 30 minutes at room temperature. The wells were washed with PBS-Tween 20 three times. Fifty μl of alkaline phosphatase-conjugated anti-mouse second antibody (available from Kirkegaard and Perry Laboratories, Gaithersburg, MD) was added (diluted 1:1000) to each well and allowed to incubate for a further 30 minutes. The excess second antibody was removed by washing with PBS-Tween 20 as before and the plates developed with alkaline phosphatase substrate/indicator (Kirkegaard and Perry Laboratories, Gaithersburg, MD) until a color change was noted. Positives developed a dark purple color after approximately 20 minutes.

The results in TABLE 2 show that *B. burgdorferi* could be detected in each of the spiked samples and that there was no interference in the assay by the 12 samples of human urine, including the two samples from patients with compromised kidney function.

TABLE 2

| Sample | O.D. 490: Spiked | Native |
|---|---|---|
| Normal 1 | .307 | .078 |
| Normal 2 | .215 | .090 |
| Normal 3 | .289 | .096 |
| Normal 4 | .345 | .102 |
| Normal 5 | .297 | .100 |
| Normal 6 | .250 | .077 |
| Normal 7 | .349 | .095 |
| Normal 8 | .457 | .110 |
| Normal 9 | .367 | .093 |
| Normal 10 | .267 | .078 |
| Transplant | .345 | .120 |
| SLE | .326 | .099 |

EXAMPLE 4

Detection of *B. burgdorferi* in the Urine of Individuals of Unknown Physical Condition Eight samples of urine from humans of unknown physical condition were assayed as described in EXAMPLE 3.

Five of the urine samples tested positive for antigens of *B. burgdorferi*. A confirmatory test was carried out on each of the five samples using the Western blot technique, i.e., by electrophoresing the samples, followed by transblotting according to the method described earlier.

Probing the blots with the monoclonal antibody demonstrated that antigens of *B. burgdorferi* were present in only two of the five samples. The positive ELISA assay results for the other three samples was presumably due to physical interference caused by clogging of the pores of the nitrocellulose membrane.

It has since been learned that such interference can frequently be avoided, e.g., by boiling the urine sample at 100° C. for 10 minutes prior to the ELISA assay in order to more thoroughly solubilize the constituents of the urine.

The two samples shown to have positive results for *B. burgdorferi* antigens were both confirmed to have come from patients with clinically-diagnosed Lyme disease. One of the patients had no serological antibody titer against *B. burgdorferi*, but showed the ECM skin lesion associated with the disease. The other patient showed no such lesion but did have a high antibody titer upon serological evaluation. The six patients providing the other samples did not in fact have Lyme disease.

I claim:

1. A method for detecting the presence of the organism *Borrelia burgdorferi* comprising the steps of:
   (a) combining a human urine sample or fraction thereof with antibodies specific for at least one antigen of said organism, wherein any of said antigen present in said urine binds to said antibodies to form an antigen-antibody complex; and
   (b) detecting the presence of said complex.

2. A method according to claim 1 wherein said antigen is selected from the group consisting of the 31,000 daltons and 34,000 daltons cellular proteins, and lipopolysaccharide of *B. burgdorferi*.

3. A method according to claim 1 wherein said antibody is monoclonal antibody.

4. A method according to claim 3 wherein said monoclonal antibody is produced by a hybridoma cell line having ATCC Accession No. HB9126.

5. A method according to claim 1 wherein said method includes electrophoresis of said urine followed by immunologically probing a transblot of the resultant gel.

6. A method according to claim 1 wherein said method is an enzyme linked immunosorbent assay.

* * * * *